United States Patent
Gaemers et al.

(10) Patent No.: US 10,935,538 B2
(45) Date of Patent: Mar. 2, 2021

(54) OIL ANALYSIS

(71) Applicant: Castrol Limited, Reading (GB)

(72) Inventors: Sander Gaemers, London (GB); Bryan Rabenau, Wayne, NJ (US); Marcel Jerusalem, Ghent (BE)

(73) Assignee: Castrol Limited, Reading (GB)

(*) Notice: Subject to any disclaimer, the term of this patent is extended or adjusted under 35 U.S.C. 154(b) by 26 days.

(21) Appl. No.: 16/302,430

(22) PCT Filed: May 16, 2017

(86) PCT No.: PCT/US2017/032915
§ 371 (c)(1),
(2) Date: Nov. 16, 2018

(87) PCT Pub. No.: WO2017/201055
PCT Pub. Date: Nov. 23, 2017

(65) Prior Publication Data
US 2019/0162711 A1    May 30, 2019

Related U.S. Application Data

(60) Provisional application No. 62/337,840, filed on May 17, 2016.

(51) Int. Cl.
*G01N 33/28* (2006.01)
*G01N 15/02* (2006.01)
(Continued)

(52) U.S. Cl.
CPC ..... *G01N 33/2888* (2013.01); *G01N 15/0227* (2013.01); *G01N 15/0643* (2013.01);
(Continued)

(58) Field of Classification Search
CPC .......... G01N 15/0227; G01N 15/0643; G01N 2015/0053; G01N 2015/0687;
(Continued)

(56) References Cited

U.S. PATENT DOCUMENTS

| | | | |
|---|---|---|---|
| 6,582,661 B1 * | 6/2003 | Pardue | G01N 33/2888 422/50 |
| 6,598,464 B1 | 7/2003 | Rossi | |

(Continued)

FOREIGN PATENT DOCUMENTS

| | | |
|---|---|---|
| EP | 1 775 571 | 4/2007 |
| FR | 2 965 924 | 4/2012 |

(Continued)

*Primary Examiner* — Hina F Ayub
(74) *Attorney, Agent, or Firm* — McDonnell Boehnen Hulbert & Berghoff LLP

(57) ABSTRACT

A method for assessing the condition of an oil using a portable computer coupled to a camera comprises: separating wear particles from a sample of the oil; capturing an image of the separated wear particles using the camera; and analysing the image and generating information about the condition of the oil using the portable computer. The method may be used for tracking the condition of an oil in a machine over a period of time. The methods are particularly useful for assessing the condition of an industrial oil e.g. a lubricating oil that has been used to lubricate moving parts in a machine.

18 Claims, 2 Drawing Sheets

(51) Int. Cl.
   *G01N 15/06*      (2006.01)
   *G01N 15/00*      (2006.01)
   *G01N 15/14*      (2006.01)

(52) U.S. Cl.
   CPC ............ *G01N 2015/0053* (2013.01); *G01N 2015/0687* (2013.01); *G01N 2015/0693* (2013.01); *G01N 2015/1486* (2013.01)

(58) Field of Classification Search
   CPC ... G01N 2015/0693; G01N 2015/1486; G01N 33/2888
   See application file for complete search history.

(56) References Cited

U.S. PATENT DOCUMENTS

| | | | | |
|---|---|---|---|---|
| 7,049,622 | B1* | 5/2006 | Weiss | G01F 23/292 |
| | | | | 250/573 |
| 2006/0267600 | A1* | 11/2006 | Beatty | F04C 29/026 |
| | | | | 324/698 |
| 2013/0191046 | A1 | 7/2013 | Henning et al. | |
| 2015/0211976 | A1 | 7/2015 | David et al. | |
| 2016/0018336 | A1 | 1/2016 | Schornstein | |
| 2016/0069856 | A1 | 3/2016 | Gorritxategi et al. | |
| 2016/0119591 | A1* | 4/2016 | Samuel | H04N 7/185 |
| | | | | 175/24 |

FOREIGN PATENT DOCUMENTS

| WO | WO 94/14049 | 6/1994 |
|---|---|---|
| WO | WO 2015/025160 | 2/2015 |

\* cited by examiner

ISO: >13/>12/>9

OIL ANALYSIS

CROSS-REFERENCE TO RELATED APPLICATIONS

This application is a National Phase application of, and claims the benefit of, International (PCT) Application No. PCT/US2017/032915, filed May 16, 2017, which claims priority to U.S. Provisional Patent Application No. 62/337,840, filed May 17, 2016, each of which is hereby incorporated by reference in its entirety.

FIELD OF THE INVENTION

The present invention relates to a method for assessing the condition of an oil. In particular, the present invention relates to a method in which information obtained from the on-site analysis of wear particles contained within an oil may be used as an indication of the condition of the oil.

BACKGROUND OF THE INVENTION

Oils such as lubricants, hydraulic fluids, compressor oils, turbine oils, metal working fluids, bunker fuels and greases are typically employed with any moving parts in a machine. Nevertheless, over time, these oils may become contaminated by particulates. Particulates include wear particles which are generated due to the friction created as parts in a machine move against one another or originate from ingress of foreign materials.

Industrial fluids are therefore frequently sampled and analysed in order to monitor the contamination level of the fluid, e.g. to determine whether the fluid needs to be replaced, or whether abnormal wear is occurring in the machine in which the fluid is used.

Wear particles found in oils include metal particles from the machine itself as well as e.g. polymeric particles from seals contained within the apparatus. Thus, chemical analysis of wear particles can provide information as to where wear is occurring within a machine.

Visual assessment of the wear particles can also provide the user with information on the wear mechanism that is occurring in a machine. Visual assessment of wear particles may involve looking at the number and morphology (e.g. shape, edge detail, size, texture, colour and thickness ratio) of the wear particles. For example, flat lamella shaped particles of 20 µm to 100 µm in length and approximately 1 µm in thickness may be indicative of delamination wear, irregularly shaped particles may be indicative of adhesive or sever wear due to direct contact between moving parts, and spherical particles of 1 µm to 5 µm in diameter may be indicative of welding wear in the machine. As a further example, the colour of a wear particle may be indicative of its composition (e.g. metallic or polymeric). The colour change of a metallic particle upon heating may also provide useful information on its composition.

Typically, a sample of an industrial fluid will be sent to a specialist laboratory for analysis by a process known as wear debris analyses (WDA). As part of the process, the sample of industrial fluid is filtered to separate the wear particles from the fluid. Filter paper having a diameter of 50 mm and a pore size of 0.8 µm is typically used.

The filter patch bearing the wear particles may then be analysed, e.g. using optical or scanning electron microscopes. The analysis may involve comparing, by a trained laboratory technician, the wear particles with reference wear particle images, such as those found within the "Wear Particle Atlas" by Daniel Anderson (published by Noria). The reference wear particle images are photographs of typical wear particles found in industrial fluids such as used lubricating oil. By comparing the wear particles with reference wear particle images, the laboratory technician may infer the mechanism by which the wear particles are being produced, e.g. they may infer the type of wear that is occurring or the parts of the machinery that are producing the wear particles. The laboratory technician may also estimate the period of time remaining until machinery failure.

However, since these methods involve off-site measurement of samples, they are expensive and time consuming, e.g. due to the cost and time involved with shipping oil samples or filter patches to the specialist laboratory. In some cases, unnecessary expenses may be incurred by sending oil samples for analysis more often than is required (around 90% of samples sent to laboratories are considered 'clean', i.e. not to contain unusual quantities or types of wear particle). In other cases, oil samples may not be sent for analysis as often as is required. This can lead to oil or machinery being changed more regularly than is necessary (out of caution) or, conversely, it can mean that oil or machinery is not changed as regularly as necessary. Moreover, the time taken to obtain the WDA analysis results means that there may be a delay in detecting on-going damage to machinery, even leading to failure which might have been avoided by quick detection of the machinery wear patterns.

In order to overcome these issues, attempts have been made to find a reliable method of analysing oil samples without the need for specialist laboratories.

Langhari et al: Automation in the Field of Wear Particles (5$^{th}$ International Conference on Information Technology and Applications, 2008) discloses the development of an automated system for classifying wear particles. The paper discloses capturing enlarged images of wear particles using a microscope and transferring the enlarged images to a desk top computer via a colour camera. An interactive image system, Wear Particle Image Analysis System (WPIAS), contained on the desktop computer is then used to analyse images of wear particles in oil samples. Although this method circumvents the requirement for the analysis to be performed using visual techniques, the use of a desktop computer prevents on-site analysis of the fluid samples.

US 2013/191046 discloses an integrated, portable sample analysis system which may be used to analyse a sample on-site. The portable analysis system comprises multiple analytical instruments, including a viscometer, a spectrometer and x-ray sub-system. Thus, the system disclosed in US 2013/191046 provides the user with a method for analysing oil samples on-site. However, the complexity of the device and the amount of analytical equipment contained therein means that such a system is not an economical method of assessing the condition of oil samples for many users.

There is a need for a method for analysing wear particles in industrial fluid samples that is more cost and time efficient than traditional methods of analysis. In particular, there is a need for a method which would enable the on-site analysis of the condition of an oil.

SUMMARY OF THE INVENTION

The present invention provides a method for assessing the condition of an oil using a portable computer coupled to a camera. The method comprises: separating wear particles from a sample of the oil; capturing an image of the separated wear particles using the camera; and analysing the image and generating information about the condition of the oil using the portable computer.

Accordingly, the present invention provides an economical method for the on-site assessment of the condition of an industrial oil. This enables the condition of the oil, and therefore the extent of wear occurring in the machine in which the oil is used, to be tracked over a period of time.

Thus, the present invention further provides a method for tracking the condition of an oil in a machine. The method comprises: taking a first sample of oil from the machine; taking a second sample of oil from the machine at a later time; assessing the condition of the first and second samples of oil using a method disclosed herein; and comparing the condition of the first and second samples of oil.

Also provided is a kit which may be used to carry out the method of the present invention. The kit comprises a syringe for holding an oil sample; a filter paper; a filter paper holder; and a container of solvent.

DETAILED DESCRIPTION OF THE PRESENT INVENTION

Figure 1A:
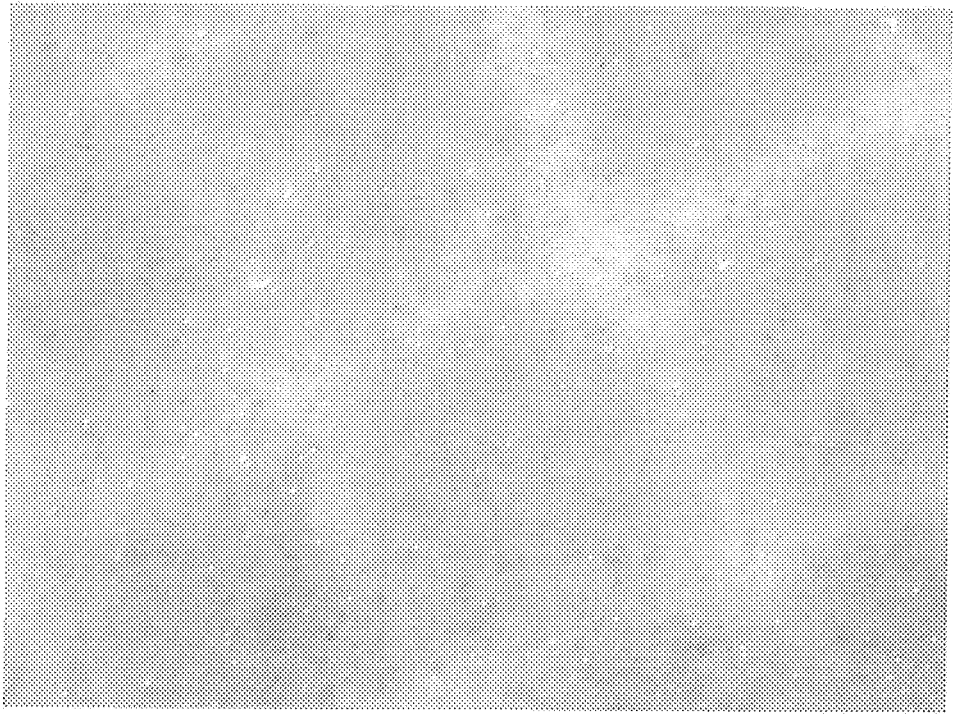
FIG. 1a is an enlarged image of wear particles which have been extracted from an oil sample.

Separating the Wear Particles from the Oil Sample

A method for analysing wear particles contained within an oil sample will now be discussed below. As part of the method, the wear particles are separated from the oil sample.

In contrast to previous methods, only a small volume of oil is required to carry out the methods disclosed herein. Thus, the oil sample may have a volume of from 0.5 ml to 100 ml. A range of from 1 ml to 50 ml may be used or a range of from 5 ml to 20 ml may be used. In some embodiments, the oil sample has a volume of 10 ml.

In preferred embodiments, the wear particles are separated from the oil sample by passing the oil sample over a filter paper. An image may then be captured of the separated wear particles that are retained on the filter paper.

The filter paper may have a pore size of from 0.5 μm to 10 μm. A range of from 1 μm to 7 μm may be used, or a range of from 2 μm to 4 μm may be used. In particular embodiments, the filter paper has a pore size of 4 μm. Although the filter paper has a larger pore size than is typically used in a laboratory, it has nonetheless been found that sufficient information may be obtained on the wear particles that are separated from the oil sample to make accurate inferences about the wear state of the machinery in which the oil has been used. Moreover, a filter paper having these pore sizes may have the oil sample passed evenly therethrough, and may reduce the tendency observed with smaller pore sizes for uneven amounts of the sample to pass through certain areas of the filter paper. Also, where the method is carried out manually by a human operator (as is preferred), the force required from the operator to pass the lubricant through a filter paper having this pore size is considered to be manageable.

The filter paper may have a diameter of from 5 mm to 50 mm. A range from 8 mm to 40 mm may be used, or a range of from 10 mm to 30 mm may be used. In some embodiments, the filter paper has a diameter of 25 mm or 13 mm, or a diameter of 13 mm. By using a filter paper with these diameters, a suitable concentration of wear particles are deposited on the filter paper for a meaningful analysis of the wear particles to be carried out.

Suitable materials for the filter paper include nitrocellulose. Since nitrocellulose filter papers are often brittle in nature, they are preferably handled with tweezers that may form part of the kits disclosed herein.

The oil sample may be passed over a filter paper by a method which comprises placing the filter paper in a filter paper holder, attaching a syringe containing the oil sample to the filter paper holder, and using the syringe to push to oil sample over the filter paper.

Before the filter paper is introduced into the filter paper holder, the surfaces of the filter paper holder are preferably washed with a solvent. The filter paper is preferably introduced while at least some of the solvent is still present on the surfaces of the filter paper holder. It is believed that the presence of solvent on the surfaces of the filter paper holder can induce capillary forces which hold the filter paper in place, thereby facilitating the accurate placement of the filter paper and reducing the likelihood of leaks, e.g. at the sides of the filter paper, as the oil sample is filtered.

The filter paper holder may comprise a funnel and a cover, with the filter paper preferably placed into the cover before the funnel is attached, e.g. by being screwed into the cover. Difficulties with balancing and centring the filter paper on the funnel are avoided by introducing the filter paper into the cover.

The filter paper holder will generally comprise an inlet, typically in the cover, for the oil sample which can e.g. be coupled to the tip of a syringe comprising an oil sample or rubber tubing through which the oil sample is transferred. The filter paper holder will also generally comprise an outlet, typically forming part of the funnel, through which the filtrate is removed. The outlet of the filter paper holder may be connected to a waste container during filtration, so that the filtrate is collected.

In some embodiments, the filter paper holder may comprise a baffle between the inlet and the filter which distributes the flow of the oil sample more evenly over the filter paper. For instance, the baffle may block the portion of the filter paper which is in line with the inlet.

Once the oil sample has passed through the filter paper, the separated wear particles which remain on the filter paper are preferably washed with a solvent. This removes residual oil sample from the surface of the filter paper and the wear particles.

The oil sample may be diluted by a solvent before it is passed through a filter paper. The solvent preferably reduces the viscosity of the oil sample. This enables easier passage of the oil sample through the filter paper. The oil sample may be diluted in a ratio of oil sample to solvent of from 20:1 to 1:10. A range of from 10:1 to 1:5, or from 5:1 to 1:2 may be used. It is convenient for a single operator to work with an oil sample having a volume of 10 ml diluted with 10 ml of solvent.

Where a syringe is used to pass the oil sample over the filter paper, the syringe may be used to extract these amounts of oil sample from a larger volume of oil. The syringe may also be used to extract the solvent which is used to dilute the oil sample.

In some embodiments, tubing may be added to the end of the syringe before extracting the oil sample. The tubing can then be submerged into the oil sample and the required amount of oil extracted into the syringe via the tubing. Preferably, the length of tubing connected to the end of the syringe is sufficient to prevent the outer surface of the syringe from being contaminated by the oil whilst the oil sample is extracted. A tube length of at least 0.1 μm is generally preferred.

In some embodiments, tubing may be added to the end of the syringe containing the oil sample. The user can then submerge the free end of the tubing into a solvent bottle in order to extract solvent into the syringe via the tubing, so as to dilute the oil sample contained therein. To prevent cross-contamination, it is preferred that different tubing is used to extract the oil sample and the solvent.

To minimise the kit that is required to carry out the methods disclosed herein, a single syringe may be used for extracting the oil sample, and for any solvent that is used to pre-wash the filter holder, dilute the oil sample or wash the separated wear particles.

Suitable solvents for pre-washing the filter holder, diluting the oil sample or washing the separated wear particles are those which are compatible with both the kit that is used to carry out the method disclosed herein and the wear particles. In particular, the selected solvent is one which does not dissolve the wear particles or cause damage to the filter paper, if used. Preferred solvents have a low flash point, low viscosity and will mix well with the oil sample (i.e. they are hydrophobic). An example of a suitable solvent is a white spirit. A single solvent is preferably used in the methods disclosed herein, as this enables just a single bottle of solvent to be provided in the kits of the present invention.

Capturing an Image of the Separated Wear Particles

Once the wear particles have been separated from the oil sample, an image of the separated wear particles is captured using the camera which is coupled to a portable computer.

The separated wear particles and, if used, the filter paper, are preferably dried before an image of the separated wear particles is captured. Typically, the separated wear particles and the filter paper will be dried through air drying. However, a heating device, e.g. a heating device which comprises a USB powered heater (such as Positive Temperature Coefficient (PTC) heater) which is powered using the portable computer, may also be used. Such heating devices speed up the drying process, and may be present in the kits of the present invention.

The camera which is used to capture an image of the separated wear particles may form part of the portable computer, i.e. the camera is coupled with the portable computer via a connection which is internal in the portable computer. In other words, the camera may form an integral part of the portable computer.

However, in preferred embodiments, the camera does not form part of the portable computer, i.e. it is coupled to the portable computer via a connection which is external to the portable computer. The image that is captured on the camera may then be transmitted to the portable computer. The camera may be coupled to the portable computer in any way, provided that they are in spatial proximity to one another, such that the camera, portable computer and all other parts of the kit may be operated by the same operator. In preferred embodiments, the camera is powered by the portable computer. In preferred embodiments, the camera and the portable computer are connected using a USB device, such a as cable. The camera and the portable computer may also be coupled wirelessly, for example, via a local area network (LAN or WLAN), wide area network (WAN), via a cellular network, or via a communication protocol such as Bluetooth, NFC (near-field communication), ZigBee and other personal or local area connections.

In preferred embodiments, the camera and the portable computer are coupled so as to enable the portable computer to act as the master and the camera to act as the slave. In these embodiments, the methods disclosed herein may involve sending instructions from the portable computer to the camera to capture an image and transmit the image back to the portable computer.

The camera may have a resolution of at least 1 megapixel. A resolution of at least 3 megapixels, or a resolution of at least 5 megapixels may also be used. In some embodiments, the camera may transmit a real-time video stream to the portable computer. This enables the operator to check that the camera is adequately positioned and focused before an image is captured.

A magnified image of the separated wear particles may be captured. A microscope may be used to magnify the separated wear particles.

The separated wear particles may be captured at magnifications of at least 50× Magnifications of at least 100×, or 150× may be used Where the camera forms part of the portable computer, the microscope may also form part of the portable computer, or it may be attached to the portable computer. This may be done by, for example, a bracket that is secured on the portable computer or via casing on the portable computer to which the microscope may be secured through screw fixing or quick release catches.

Where the camera does not form part of the portable computer, then the microscope and camera may form part of the same device which may, for example, be powered by the portable computer. An example of a suitable device is the Celestron® Digital Microscope Pro, a low-power 20× to 200× microscope with a 5.0 megapixel sensor for capturing photos and video.

The wear particles are preferably illuminated in the image. This may be achieved using a microscope which comprises one or more sources of light, for example, LEDs. The separated wear particles may be backlit, though they are preferably lit from the front. A distributed lighting system, such as a ring of LED lights centred around the wear particles to be captured in an image, is particularly suitable as this reduces the shadows that may be cast from the wear particles on the filter paper. Alternatively the lighting source may be part of the portable computer (the light source of a mobile data device) or the flash of a camera.

Images of separated wear particles on a filter paper are preferably obtained from the side through which the oil sample was passed. However, images may also be taken from the underside of the filter paper. Since oxidised oil and additives leave a yellow residue on the underside of the filter paper, images taken of the underside of the filter paper are useful for determining the level of oxidation which has taken place through the intensity of the yellowing of the filter paper.

Where a filter paper has been used to separate the wear particles from the oil sample, then typically only a portion of the surface of the filter paper will be captured in the image. An image of a portion of the filter paper having an area of from 0.1 to 20 mm$^2$ is captured, although an area of from 0.5 to 10 mm$^2$, or from 0.5 to 3 mm$^2$ may be used.

In embodiments where only a portion of the surface of the filter paper is captured in an image, the optical axis of the camera is preferably offset from the centre of the filter paper. More of the oil sample may pass through the centre of the filter paper, for example, when the sample is pushed through the filter paper using a syringe. Therefore an image of a patch of the filter paper that is offset from the centre of the filter paper may contain a more representative sample of wear particles than an image of the centre of the filter paper.

In some embodiments, at least two images of the separated wear particles are captured and analysed to determine information about the wear particles. Each of these images preferably captures different wear particles that have been separated from the oil sample (the images are taken of different parts of the filter paper). For instance, images of the filter paper may be captured at non-overlapping locations offset from the centre of the filter paper. All of the images obtained are analysed, thereby improving the accuracy of the method.

In some embodiments, a sample holder is used to hold the filter paper when the image is captured. The sample holder may comprise a stage which allows the filter paper to be moved and/or rotated by a set amount, such that multiple images of the filter paper may be taken. Preferably, the sample holder or the portable computer indicates to the user when the filter paper has been moved and/or rotated by a set amount (for example a predetermined number of degrees) relative to its previous position. This prevents the user from analysing images containing the same portion of the filter paper more than once.

Analysing the Image

Once the image of the separated wear particles has been captured, it may be analysed using the portable computer. The portable computer may then generate information about the condition of the oil.

Any portable computer may be used to analyse the image of the separated wear particles and generate information about the condition of the oil. A portable computer can be carried by a single person, (in a bag or case, for example). Suitable portable computers include laptops, tablets and mobile data devices, including mobile phones and smart phones. Preferably, the portable computer is a mobile data device. A processor in the portable computer may be used to analyse the image and generate information about the condition of the oil. Suitable software for use on the processor includes image recognition software, which is able to recognise, identify and/or detect the presence of wear particles in a sample of oil.

The image is preferably analysed by a process in which the separated wear particles are identified in the image; and one or more features of the identified wear particles are determined. The one or more features of the identified wear particles may be selected from the size, shape, edge detail, number and colour of the wear particles. Preferably, the image is analysed by a process which involves determining the size and number of the wear particles. Once the number of wear particles (e.g. of a particular size) has been determined, the concentration of wear particles in the oil may be back-calculated from the volume of the oil sample, the filter paper area and the proportion of the filter paper area that has been captured in an image and analysed.

The separated wear particles may be identified in the image by converting the image, or a copy thereof, into a monochrome image, identifying the most prevalent shade(s) and assigning this as the filter paper, and identifying the wear particles as those portions of the monochrome image which are lighter or darker than the filter paper. In preferred embodiments, the original or the monochrome image may be modified so that the boundaries of the identified wear particles are marked. Features of the wear particles may then be determined based on the marked boundaries. Known image processing techniques such greyscale matching and edge detection may be employed in the analysis process.

Information that is generated about the condition of the oil is inferred based on the features of the wear particles. One method of doing this is to compare the captured images with reference images of wear particles from oils that have undergone specific wear lifetimes or experienced known wear conditions. Image comparison techniques may be used to compare specific features of the wear particles in order to identify wear times and causes. Such reference images may be stored in a database accessible by the portable computer either by being stored in a memory device associated with the portable computer or remote from the portable computer (for example at a server or utilising cloud storage). The larger the number of reference images stored in the database and accessible to the user the more accurate the analysis is likely to be.

Information about the condition of the oil may relate to the cleanliness of the oil. For instance, the information may relate to the wear particle concentration, such that the information may be in the form of a graph of wear particle size concentration. Information may also be provided in the form of a coding system, e.g. an industry standard coding system. The coding system may indicate the number of particles falling within one or more, e.g. two or preferably three, size range per millilitre of oil. One possible coding system is based on ISO classification 4406:1999, according to which a three number code of the form "NN/NN/NN" represents the number of particles having a size of $\geq 4$ µm/$\geq 6$ µm/$\geq 14$ µm per millilitre of oil. More basic coding systems include traffic light systems in which a green light indicates that the oil is relatively clean, amber indicates that the oil is slightly contaminated, and red indicates that the oil is contaminated and requires replacement.

Information about the condition of the oil may also relate to the condition of the machine in which the oil is used. For instance, the information may relate to the amount of wear occurring, the type of wear occurring, or the location of the wear occurring. This could be in the form of information on the material type or composition of the wear particles produced.

The information which is generated about the condition of the oil is in the form of an instruction to a user or an operator. For instance, the instruction may be: to change or clean the oil; to change or clean the machinery or a part of the machinery (in which the oil is being used); to send the oil to a laboratory for further testing; to carry out further testing on the machinery in which the oil is being used; or to retest the oil at a set time in the future. The method may also comprise carrying out the instructions.

Information generated about the condition of the oil, including information in the form of instructions, is preferably output through a display on the portable computer. However information may be output in the form of executable programme steps if the operation conditions of the machinery require any alteration.

The method of the present invention preferably involves inputting one or more further details about the sample of oil into the portable computer. The one or more further details preferably relate to the nature of the oil or the conditions in which the oil has been used. For instance, the one or more further details may include:

the brand, range and grade (including both or one of the viscosity and lubricant grades) of the oil;
the make, model and part of the machine in which the oil has been used;
the geographical location in which the oil has been used;
the date of the last oil change or oil top-up; and
the date that the sample was taken.

By inputting one or more further details about the sample of oil into the portable computer, information about the condition of the oil may be generated by comparing the wear particles to a subset of oils of a known condition, the subset of oils being selected based on the one or more further details of the oil sample. The subset of oils may be selected because they are similar in nature or have been used under similar conditions to the oil sample.

In some embodiments, the method comprises updating a database which contains information on the condition of used oils with the results of the analysis of the image of the separated wear particles, and the further details of the oil sample that were inputted into the portable computer. This enables an improved database on the condition of used oils to develop over time.

The method may be repeated using oil samples that have been taken from a machine over a period of time. Accordingly, a method of tracking the condition of an oil in a machine is also provided. The method involves taking a first sample of oil from the machine and, at a later time, taking a second sample of oil from the machine. The condition of the first and second samples of oil may then be assessed using the method described herein, and compared. In this way, information about how the machine and oil are performing over time may be gleaned.

In some embodiments, the condition of the oil over time may be represented graphically. This enables the operator to readily identify any changes in the condition of the oil.

When using a portable computer device, such as a mobile data device, to perform the method described above, it may be desirable to use specific application software (commonly known as an "App"), downloadable from a central store or server, that carries out the method steps in communication with any camera, microscope or other device coupled to the portable computer. Such software may be in the form of a computer program stored on a non-transient storage device, or other readable medium, such that when run on the portable computer causes it to perform any of the method steps outlined above.

Oils

The oil that is assessed using the methods disclosed herein may be any industrial oil. Since the condition of the oil is assessed to determine wear, then it will be appreciated that the oil will generally be a used oil. Alternatively, a clean unused oil may be assessed to provide a more accurate base condition to compare future samples with. The method is particularly suited for assessing the condition of an oil which has been used in a machine e.g. a lubricating oil that has been used to lubricate moving parts in a machine.

Oil which may be assessed includes: engine oils; gearbox oils; hydraulic oils; compressor oils; turbine fluids; and bunker fuels. Other lubricating oils may also be assessed.

Kit

A kit which contains the apparatus that is necessary for carrying out the methods disclosed herein is also provided. The kit comprises a syringe for holding an oil sample, a filter paper, a filter paper holder, and a container of solvent. Preferably, at least two filter papers are provided in the kit, so that multiple samples may be assessed. Similarly, at least two syringes are also preferably provided in the kit, one for each filter paper.

The kit may further comprise a camera which is suitable for coupling to a portable computer. The camera may be integrated in a portable computer, in which case the kit comprises a portable computer comprising a camera. However, as detailed above, it is preferred that the camera is not integrated into a portable computer. In these embodiments, it is assumed that the user will have a portable computing device, such as a mobile data device, which can be coupled with the camera. The camera preferably forms part of a device which also comprises a microscope for magnifying the wear particles. However, the microscope or suitable lens arrangement may be a separate component mountable on the camera.

The kit preferably also comprises one or more of, and preferably all of:
rubber tubing for connecting the syringe to the filter paper holder;
tweezers for handling the filter paper;
a waste bottle for collecting used solvent and filtered oil; and
a sample holder for holding the filter paper when an image of the filter paper is captured using the camera.

The kit may further comprise other components that are disclosed herein for use in the methods of the present invention.

In preferred embodiments, the kit comprises a housing such as a case or suitcase in which the apparatus is held. The kit is advantageously both low-cost and portable.

The present invention will now be described by reference to the following non-limiting examples.

EXAMPLES

Example 1: Separating Wear Particles from an Oil Sample

A filter paper holder comprising a funnel and a cover was washed with white spirit. A filter paper, 13 mm in diameter and having a pore size of 3 µm, was inserted into the wet cover using tweezers, and the funnel then screwed into the cap.

A 10 ml sample of used gear oil and 10 ml of white spirit was extracted into a syringe via rubber tubing. The rubber tubing was attached to an inlet in the cover of the filter paper holder. An outlet in the funnel of the filter paper holder was attached to the inlet of a waste container. The syringe was used to push the diluted oil sample through the filter paper.

The filter paper was washed with a further 10 ml of white spirit, extracted and delivered using the syringe and optionally rubber tubing.

The filter paper was removed from the filter paper holder and placed on a sample holder. The filter paper was left to air dry for about 10 minutes.

Example 2: Capturing an Optical Image of the Separated Wear Particles

A Celestron® Digital Microscope Pro was attached to a mobile phone via a USB device. The microscope was positioned over the filter paper and instructions were sent from the mobile phone to the camera to capture an image and transmit the image back to the mobile phone. The separated wear particles were illuminated by a distributed light source when the image was captured.

Figure 1B:
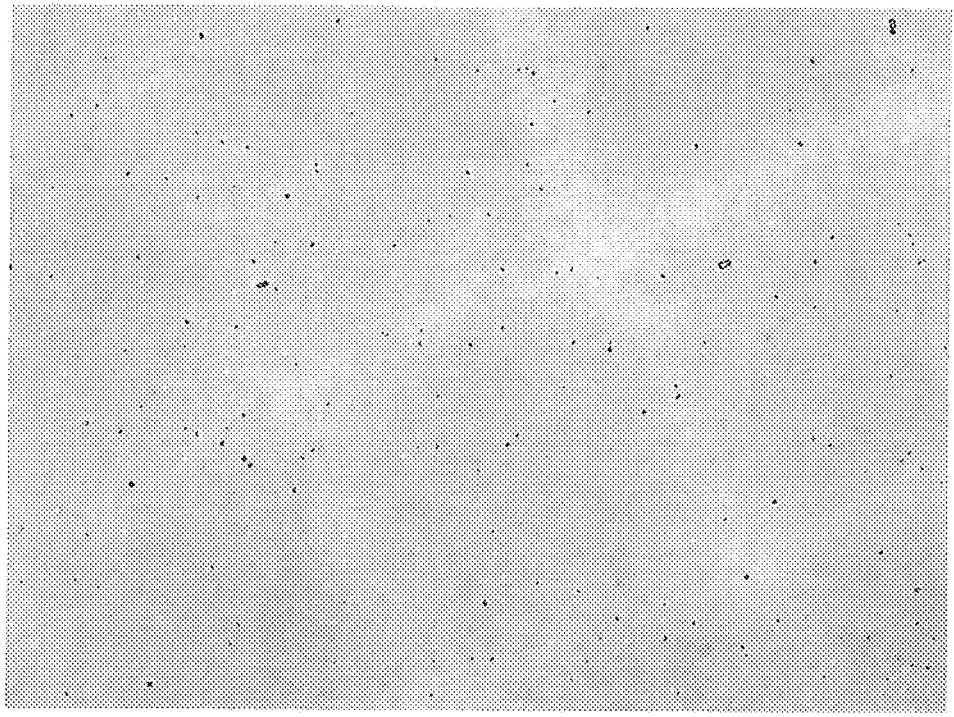
FIG. 1b shows the enlarged image of FIG. 1a after software on a mobile phone has marked the presence of wear particles.

Example 3: Analysing the Image of the Oil, and Generating Information about the Condition of the Oil The image was analysed using the mobile phone by a process in which the separated wear particles were identified and marked in the image. FIG. 1a shows the image taken by the camera; and FIG. 1b shows the image after wear particles have been identified and marked using the software application run on the processor of the mobile phone. Features including the size and number of the identified wear particles were determined.

Figure 2A:
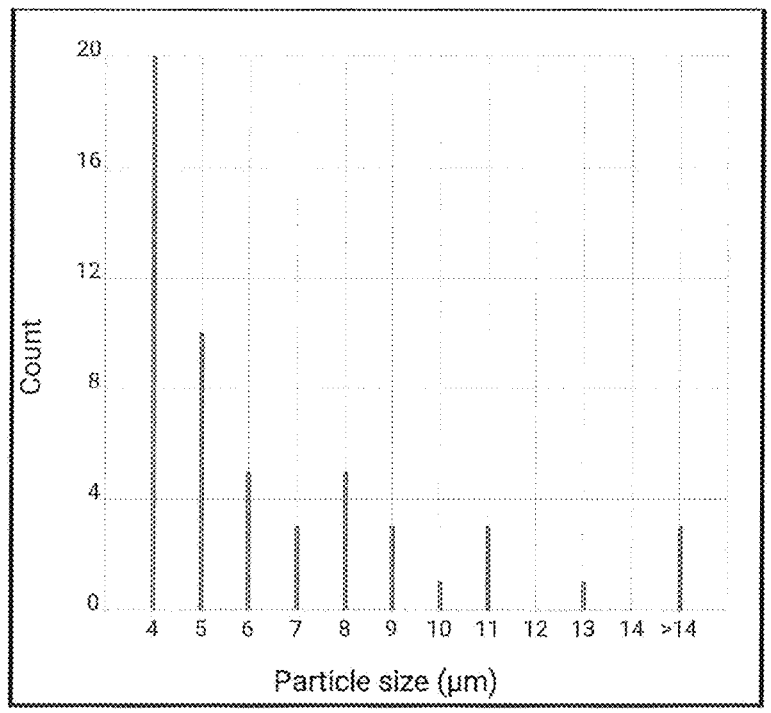
FIG. 2a is a graph showing the size distribution of the identified wear particles in the oil sample.
Figure 2B:
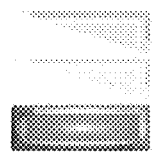
FIG. 2b shows the ISO classification determined for the oil sample using the analysis method of the present invention, and a traffic light coding system which indicates that the oil was in good condition.

Information on the cleanliness of the oil was output through a display on the mobile phone. FIG. 2a shows a graph of the number of particles of different sizes contained within the oil sample that was output through a display on the mobile phone. FIG. 2b shows the ISO classification that the oil sample was calculated to have from the image, and that was also output through a display on the mobile phone. A traffic light coding system, shown to the right of FIG. 2b, was further displayed. In this case, the green (lowermost) traffic light was shown, indicating that the oil was in good condition.

The invention claimed is:

1. A method for assessing the condition of an oil using a portable computer coupled to a camera, said method comprising:
   separating wear particles from a sample of the oil;
   capturing an image of the separated wear particles using the camera;
   analyzing the image, using the portable computer, by identifying the separated wear particles in the image and determining one or more features of the identified wear particles, wherein identifying the separated wear particles in the image comprises:
      identifying a prevalent shade from a plurality of shades of the image; and
      identifying the wear particles as portions of the image which are a lighter shade than the prevalent shade or a darker shade than the prevalent shade;
   determining information about the condition of the oil using the portable computer; and
   generating an instruction based on the determined information about the condition of the oil using the portable computer, wherein the instruction comprises an instruction: (i) to send the oil to a laboratory for further testing, or (ii) to carry out further testing on the machinery in which the oil is being used.

2. The method of claim 1, wherein the wear particles are separated from the oil sample by passing the oil sample over a filter paper, and capturing an image of the separated wear particles on the filter paper.

3. The method of claim 2, wherein the filter paper has a pore size of from 0.5 μm to 10 μm.

4. The method of claim 2, wherein the filter paper has a diameter of from 5 mm to 50 mm.

5. The method of claim 2, wherein the centre of the filter paper is offset from the optical axis of the camera.

6. The method of claim 1, wherein capturing the image of the separated wear particles comprises capturing a magnified image.

7. The method of claim 1, wherein capturing the image of the separated wear particles comprises capturing at least two images of the separated wear particles.

8. The method of claim 1, wherein capturing the image of the separated wear particles comprises illuminating the separated wear particles using a distributed light source.

9. The method of claim 1, wherein information about the condition of the oil may be generated by comparing the features of the identified wear particles with information about features of wear particles within an oil sample of a known condition.

10. The method of claim 1, wherein information generated about the condition of the oil relates to the cleanliness of the oil, or the condition of the machinery in which the oil was used.

11. The method of claim 1, wherein the method comprises inputting one or more further details about the sample of oil into the portable computer.

12. The method of claim 11, wherein the one or more further details are used to update a database which contains information on the condition of oils.

13. The method of claim 1, wherein the oil has been used in a machine.

14. A computer program stored on a non-transient storage medium, which when run on a portable computer causes the portable computer to carry out the method of claim 1.

15. A method for tracking the condition of an oil in a machine, said method comprising:
   taking a first sample of oil from the machine;
   taking a second sample of oil from the machine at a later time; and
   assessing the condition of the first and second samples of oil using a method in accordance with claim 1; and
   comparing the condition of the first and second samples of oil.

16. The method of claim 1, further comprising:
   drying the separated wear particles and the filter paper by way of a heating device.

17. The method of claim 1, wherein the instruction further comprises an instruction to change or clean the oil, to change or clean the machinery or a part of the machinery in which the oil is being used, or retest the oil in the future.

18. The method of claim 1, further comprising:
   Outputting the instruction through a display on the portable computer.

* * * * *